(12) United States Patent
Triplett et al.

(10) Patent No.: US 7,504,539 B2
(45) Date of Patent: *Mar. 17, 2009

(54) PROCESS FOR PREPARING 4-AMINODIPHENYLAMINE INTERMEDIATES

(75) Inventors: Ralph D. Triplett, Wadworth, OH (US); Roger Keranen Rains, Richfield, OH (US)

(73) Assignee: Flexsys America LLP, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/639,945

(22) Filed: Dec. 15, 2006

(65) Prior Publication Data

US 2007/0191641 A1 Aug. 16, 2007

Related U.S. Application Data

(63) Continuation of application No. 10/444,524, filed on May 23, 2003, now Pat. No. 7,183,439.

(60) Provisional application No. 60/432,285, filed on Dec. 10, 2002.

(51) Int. Cl.
*C07C 209/60* (2006.01)

(52) U.S. Cl. ............... 564/416; 564/420; 564/421; 564/422; 564/423; 564/433; 564/434

(58) Field of Classification Search ............... None
See application file for complete search history.

(56) References Cited

U.S. PATENT DOCUMENTS 4,463,191 A   7/1984  D'Sidocky et al. ........... 564/398
5,117,063 A   5/1992  Stern et al. ................... 564/398
5,608,111 A   3/1997  Stern et al. ................... 564/398
5,612,483 A   3/1997  Jautelat ....................... 544/332
5,739,403 A   4/1998  Reinartz et al. .............. 564/423
6,140,538 A   10/2000 Rains et al. .................. 564/416
6,395,933 B1  5/2002  Triplett, II et al. ........... 564/420
6,583,320 B2  6/2003  Triplett, II et al. ........... 564/420
7,183,439 B2  2/2007  Triplett, II et al. ........... 564/416

FOREIGN PATENT DOCUMENTS

EP   0 566 783 A1     10/1993
WO   WO 00/35853 A1   6/2000
WO   WO 01/14312 A1   3/2001
WO   WO 02/34372 A2   5/2002

OTHER PUBLICATIONS

Ankur A. Banerjee and Doble Mukesh, "Heterogeneous Catalytic Tranfer Hydrogenation of 4-Nitrodiphenylamine to p-Phenylenediamines," *J. Chem Soc., Chem. Commun.*, 1998, 1275-1276.

*Primary Examiner*—Brian J Davis
(74) *Attorney, Agent, or Firm*—Brinks Hofer Gilson & Lione

(57) ABSTRACT

The invention is directed to a method of producing one or more 4-aminodiphenylamine intermediates comprising the steps:
  a. bringing an aniline or aniline derivative and nitrobenzene into reactive contact; and
  b. reacting the aniline and nitrobenzene in a confined zone at a suitable time and temperature, in the presence of a mixture comprising a strong organic base, or equivalent thereof, and an oxidant comprising hydrogen peroxide in an amount of from about 0.01 to about 0.60 moles of hydrogen peroxide to moles of nitrobenzene.

28 Claims, 5 Drawing Sheets

PROCESS FOR PREPARING 4-AMINODIPHENYLAMINE INTERMEDIATES

CROSS REFERENCE TO RELATED APPLICATIONS

This application is a continuation of U.S. patent application Ser. No. 10/444,524, filed May 23, 2003, now U.S. Pat. No. 7,183,439 B2, entitled "Process for Preparing 4-Aminodiphenylamine Intermediates," which is incorporated herein by reference in its entirety; which, in turn, claims priority of U.S. Provisional Patent Application No. 60/432,285, filed Dec. 10, 2002 and 60/446,621, filed Feb. 11, 2003, the entire contents of which are incorporated herein by reference.

BACKGROUND OF INVENTION

1. Field of Invention

The present invention relates to a process for preparing 4-aminodiphenylamine intermediates.

2. Related Art

4-Aminodiphenylamines are widely used as intermediates in the manufacture of alkylated derivatives having utility as antiozonants and antioxidants, as stabilizers for monomers and polymers, and in various specialty applications. For example, reductive alkylation of 4-aminodiphenylamine (4-ADPA) with methylisobutyl ketone provides N-(1,3-dimethylbutyl)-N'-phenyl-p-phenylene-diamine, which is a useful antiozonant for the protection of various rubber products.

4-Aminodiphenylamine derivatives can be prepared in various ways. An attractive synthesis is the reaction of an optionally substituted aniline with an optionally substituted nitrobenzene in the presence of a base, as disclosed, for example, in U.S. Pat. No. 5,608,111 (to Stern et al.) and U.S. Pat. No. 5,739,403 (to Reinartz et al.). U.S. Pat. No. 5,608,111 describes a process for the preparation of an optionally substituted 4-ADPA wherein in a first step optionally substituted aniline and optionally substituted nitrobenzene are reacted (coupled) in the presence of a base. In working examples, aniline and nitrobenzene are reacted in the presence of tetramethylammonium hydroxide as the base, and water and aniline are azeotropically removed during the coupling reaction.

International publication WO 00/35853 discloses a method of preparation of intermediates of 4-aminodiphenylamine by the reaction of aniline with nitrobenzene in a liquid medium where the reaction system consists of a solution of salts of true zwitterions with hydroxides. A combination of potassium hydroxide and betaine hydrate is exemplified. The reaction may take place in the presence of free oxygen.

EP publication 566 783 describes a method of manufacture of 4-nitrodiphenylamine by the reaction of nitrobenzene with aniline in the medium of a polar aprotic solvent in a strongly alkaline reaction system. A phase transfer catalyst such as tetrabutylammonium hydrogen sulfate is employed. This reference requires that the reaction be carried out in an oxygen-free atmosphere in order to prevent undesirable side reactions caused by oxidation.

U.S. Pat. No. 5,117,063 and International publication WO 01/14312 disclose processes for preparing 4-nitrodiphenylamine and 4-nitrosodiphenhylamine, using various bases, including tetraalkylammonium hydroxides alone or an inorganic base with crown ether as a phase transfer catalyst. The use of aerobic conditions is described, including by example. Less azobenzene is reported for reactions at anaerobic conditions with aniline as the solvent or at aerobic conditions with DMSO, and other similar solvents, as the solvent.

U.S. Pat. No. 5,612,483 describes a process for preparing nitro substituted arylamines, including 4-nitro-diphenylamine, comprising reaction of an aryl amine with a nitroaryl amine, in the presence of bases while introducing oxygen in polar solvents. The patent states that the reactions lead to good yields of the corresponding amines with the use of simple bases, preferably inorganic bases.

U.S. Pat. No. 6,140,538 describes a process for preparing an optionally substituted 4-aminodiphenylamine comprising reacting an optionally substituted aniline and an optionally substituted nitrobenzene in the presence of water and a base while controlling the water content so as to ensure a molar ratio of water to the base charged of not less than about 4:1 at the start of the coupling reaction and not less than about 0.6:1 at the end of the coupling reaction to produce 4-nitrodiphenylamine and/or 4-nitrosodiphenylamine and/or salts thereof. The coupling reaction is followed by a hydrogenation reaction where the coupling reaction product is hydrogenated in the presence of a hydrogenation catalyst and added water so as to ensure a molar ratio of total water to base of at least about 4:1 at the end of hydrogenation. Aqueous and organic phases are obtained and the optionally substituted 4-aminodiphenylamine is recovered from the organic phase and the aqueous phase containing the base is recycled.

U.S. Pat. No. 6,395,933 describes a process for producing one or more 4-aminodiphenylamine intermediates comprising the steps of bringing an aniline or aniline derivative and nitrobenzene into reactive contact; and reacting the aniline and nitrobenzene in a confined zone at a suitable time and temperature, in the presence of a mixture comprising a strong base, a suitable phase transfer catalyst and an oxidant. Certain phase transfer catalysts may also function as the strong base, such as tetraalkylammonium hydroxides. Examples are given that show increased selectivity for reactions in the presence of air or hydrogen peroxide, with KOH as the strong base and tetramethylammonium chloride as the phase transfer catalyst. The example with hydrogen peroxide does not indicate an optimum amount of peroxide in going from a mole ratio of $H_2O_2/NB=0$ to 1.0, whereas conversion steadily dropped as mole ratio increased. No examples were given for an oxidant with a phase transfer catalysts that also functions as the strong base.

The objective of the present invention is to provide a superior method for producing one or more 4-ADPA intermediates by reacting aniline and nitrobenzene in the presence of a strong organic base, or equivalent thereof, and an oxidant comprising hydrogen peroxide.

SUMMARY OF THE INVENTION

In brief summary, the primary embodiment of the present invention is for a method of producing one or more 4-aminodiphenylamine intermediates comprising the steps of:
  a. bringing an aniline or aniline derivative and nitrobenzene into reactive contact; and
  b. reacting the aniline and nitrobenzene in a confined zone at a suitable time and temperature, in the presence of a mixture comprising a strong organic base, or equivalent thereof, and an oxidant comprising hydrogen peroxide in an amount of from about 0.01 to about 0.60 moles of hydrogen peroxide to moles of nitrobenzene.

Other embodiments of the present invention encompass details about reaction mixtures, ratios of ingredients, particular strong organic bases and reaction conditions, all of which

DETAILED DESCRIPTION OF THE INVENTION

Figure 1:
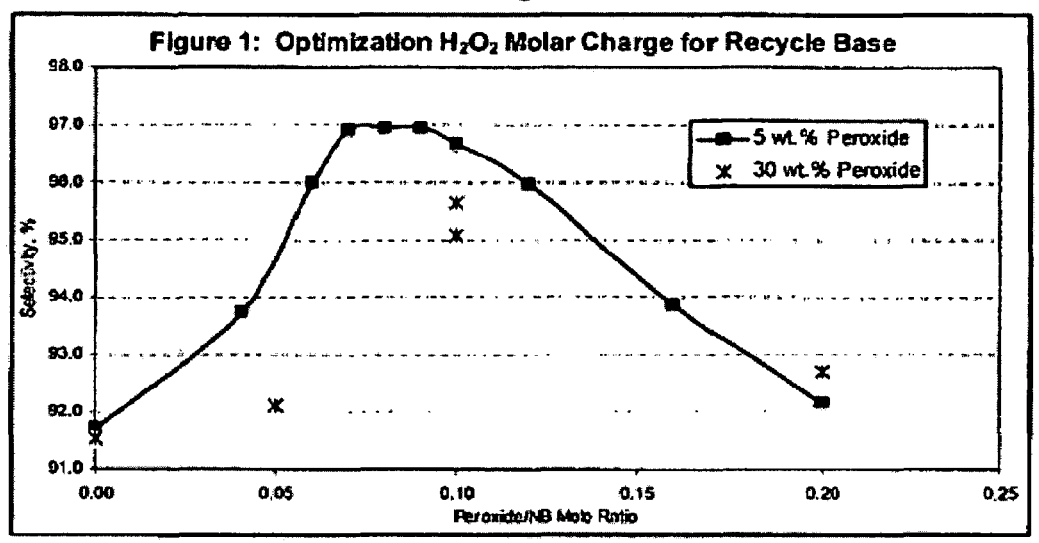
FIG. 1 is a graph showing the optimization $H_2O_2$ molar charge for recycle base based on Example 8.

The present invention is directed to a method, as described above, for making intermediates of 4-ADPA that has superior yield and selectivity for those intermediates. Such intermediates comprise 4-nitroso- and/or 4-nitrodiphenylamines (p-NDPA and 4-NDPA, respectively) and salts thereof. The intermediates may then be hydrogenated to produce 4-aminodiphenylamine.

While aniline most effectively couples with nitrobenzene, certain aniline derivatives comprising amides such as formanilide, phenylurea and carbanilide as well as thiocarbanilide, or mixtures thereof, can be substituted for aniline or used in conjunction with aniline to produce 4-ADPA intermediates.

Although the reactants of the method of the invention are referred to as "aniline" and "nitrobenzene", and when it is 4-ADPA that is being manufactured the reactants are in fact aniline and nitrobenzene, it is understood that the reactants may also comprise substituted aniline and substituted nitrobenzene. Typical examples of substituted anilines that may be used in accordance with the process of the present invention include but are not limited to 2-methoxyaniline, 4-methoxy-aniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene, and mixtures thereof. Typical examples of substituted nitrobenzenes that may be used in accordance with the process of the present invention include but are not limited to o- and m-methylnitrobenzene, o- and m-ethylnitrobenzene, o- and m-methoxynitrobenzene, and mixtures thereof.

The molar ratio of aniline to nitrobenzene in the process according to the present invention is not particularly important, the process will be effective with an excess of either.

In the method of the invention, the hydrogen peroxide may be supplied as an aqueous solution comprising from about 3 wt. % to about 50 wt. % hydrogen peroxide.

The intermediates of the invention may be reduced to produce 4-aminodiphenylamine. The reduction can be carried out by any known method, including the use of hydrogen that involves the use of a hydrogenation catalyst. Details concerning choice of catalyst and other aspects of the hydrogenation reaction, such as the addition of water, may be found in U.S. Pat. No. 6,140,538. Hydrogenation end points can be determined by the reaction time and/or the hydrogen flow profile and/or by one of various instrumental techniques that are known to one skilled in the art. Other means of reduction that do not involve the direct use of hydrogen and are known to one skilled in the art, can also be used to reduce the 4-ADPA intermediates or substituted derivatives thereof to 4-ADPA or substituted derivatives thereof.

The 4-aminodiphenylamine produced may be reductively alkylated to an alkylated derivative of the 4-aminodiphenylamine, which are useful for the protection of rubber products, in which process an optionally substituted aniline and an optionally substituted nitrobenzene are coupled and subsequently reduced according to the invention process, after which the 4-aminodiphenylamine so obtained is reductively alkylated to an alkylated derivative of the 4-aminodiphenylamine according to methods known to the person skilled in this technical field. Typically, the 4-ADPA and a suitable ketone, or aldehyde, are reacted in the presence of hydrogen and platinum-on-carbon as catalyst. Hydrogenation end points can be determined by the reaction time and/or the hydrogen flow profile and/or by one of various instrumental techniques that are known to one skilled in the art. Suitable ketones include methylisobutyl ketone, acetone, methylisoamyl ketone, and 2-octanone. See for example U.S. Pat. No. 4,463,191, incorporated herein by reference and Banerjee et al, J. Chem. Soc. Chem. Comm. 18, 1275-1276 (1988). Suitable catalysts can be the same as, but not limited to, those described above for obtaining the 4-ADPA.

Hydrogen peroxide is a superior oxidant to air, as the amount of air required to get a meaningful increase in selectivity would greatly overload any commercially economical condenser system, resulting in high losses of organic compounds through the condenser. Moreover, even though pure oxygen would be more efficient than air, the use of pure oxygen creates an unsafe reaction environment. In addition, hydrogen peroxide does not require a solvent other than excess aniline.

The oxidant may be introduced into the confined zone after the start of nitrobenzene being introduced into the confined zone, or the introduction of the oxidant into the confined zone may be completed before the completion of nitrobenzene being introduced into the confined zone, or both.

The nitrobenzene and aniline react to form a Meisenheimer complex and the oxidant is optimally introduced into the confined zone at the point where the concentration of said Meisenheimer complex is the highest. The oxidant may be fed at a variable rate such as to optimally match the reaction kinetics for formation and disappearance of the Meisenheimer complex made from nitrobenzene and aniline. The point of entry of the oxidant into the confined zone may be at or near the point of entry of nitrobenzene.

Coupling of aniline with nitrobenzene in the presence of a base proceeds via a Meisenheimer complex, which undergoes intramolecular oxidation to p-NODPA salt and intermolecular oxidation by nitrobenzene, and some process impurities, to 4-NDPA salt. Peroxide improves selectivity by oxidizing the complex faster than nitrobenzene and the impurities do and by oxidizing the complex preferentially to oxidizing aniline. Thus any process variable that affects the rates of Meisenheimer formation and intramolecular oxidation, such as impurity levels in recycle streams, reaction temperature, water removal rate and nitrobenzene feed rate will affect the optimum peroxide mole ratio and the effective range for peroxide. Furthermore, peroxide concentration can affect the localized selectivity for peroxide reacting with Meisenheimer vs. aniline. So although an effective range of $H_2O_2/NB=0.01-0.2$ is illustrated by example for a particular reaction procedure with recycle base, and as wide as 0.01-0.46 with fresh base, it is envisaged that conditions can be found for which the effective range is as wide as $H_2O_2/NB=0.01-0.6$. In addition, reaction profiles show that nitrobenzene reacts rapidly at the start, when base level is highest, and more slowly near the end, when base level is lowest. Therefore, an alternative procedure for peroxide is to delay the start of peroxide and end it early, while adding it at a fixed or variable rate when nitrobenzene reaction rate is in the mid range. Another alternative procedure is to add peroxide throughout, but more slowly at the start and end. Yet another alternative procedure is to vary peroxide addition rate throughout. The process of the invention is meant to apply to fresh base, recycle base, recycle base that has been recovered by electrolysis, such as described in WO 2002034372, incorporated herein by reference, or by any other procedure, and to mixtures thereof.

In order to get the highest efficiency for the use of hydrogen peroxide, peroxide should be fed into the reactor at the point where the concentration of the Meisenheimer complex made from aniline and nitrobenzene is the highest. This gives peroxide the maximum opportunity to react with Meisenheimer instead of with aniline. It can be expected that the optimum point of entry for peroxide in a commercial reactor should be at or near the point of entry of nitrobenzene, since Meisenheimer concentration should be highest there. However, depending on the configuration and operation of a commercial reactor, the optimum point of entry can vary somewhat, which can be determined by one skilled in the art.

A big advantage for the use of peroxide in the method of the invention is that there is a great reduction of the amount of azobenzene that has to be hydrogenated to aniline for recycle, as compared to a process without peroxide. For an existing 4-ADPA commercial facility, this translates to a significant amount of excess capacity for an aniline recovery (from azobenzene) operation. This excess capacity can be utilized by feeding nitrobenzene to the azobenzene hydrogenation reactor to generate some aniline, which is a more expensive raw material for the process of the invention. For a new 4-ADPA facility, the greatly reduced azobenzene quantity can translate to a significant capital reduction for the aniline recovery (from azobenzene) system. Alternatively, it can translate to a modest capital investment for a system that can convert both nitrobenzene and azobenzene to aniline for recycle.

Strong organic bases particularly effective in the method of the present invention include quaternary ammonium hydroxide selected from the group consisting of tetramethylammonium hydroxide, tetrabutylammonium hydroxide, methyltributylammonium hydroxide, benzyltrimethylammonium hydroxide, tricaprylmethylammonium hydroxide, cetyltrimethylammonium hydroxide and choline hydroxide and equivalent quaternary ammonium alkoxides, acetates, carbonates, bicarbonates, cyanides, phenolics, phosphates, hydrogen phosphates, hypochlorites, borates, hydrogen borates, dihydrogen borates, sulfides, silicates, hydrogen silicates, dihydrogen silicates and trihydrogen silicates.

A preferred organic base is tetramethylammonium hydroxide.

The intermediates may be reduced to produce 4-aminodiphenylamine and base may be recycled from the products of the reduction reaction, alone or with make-up quantities of fresh base or purified recycle base or both, for use in the reaction of the method of the invention. More specifically, the intermediates may be reduced to produce 4-aminodiphenylamine, and base in the products of the reduction reaction may be purified to remove some or all of the quaternary ammonium salt impurities formed in the reactions of the coupling reaction of the method of the invention and reduction reaction. The purified base may be recycled, as the sole base or in combination with unpurified recycle base and/or together with make-up quantities of fresh base.

The reactive contact of the process of the invention is carried out in the presence of an oxidant comprising hydrogen peroxide. When the organic base is tetramethylammonium hydroxide, the hydrogen peroxide may be supplied as an aqueous solution comprising from about 3 wt. % to about 50 wt. % hydrogen peroxide, or, more preferred, as an aqueous solution comprising from about 3 wt. % to about 7 wt. % hydrogen peroxide in an amount of from about 0.01 to about 0.5 moles of hydrogen peroxide to moles of nitrobenzene. More preferred is that the hydrogen peroxide be supplied as an aqueous solution comprising from about 15 wt. % to about 25 wt. % hydrogen peroxide in an amount of from about 0.01 to about 0.45 moles of hydrogen peroxide to moles of nitrobenzene. Most preferred is that the hydrogen peroxide be supplied as an aqueous solution comprising from about 25 wt. % to about 40 wt. % hydrogen peroxide in an amount of from about 0.01 to about 0.35 moles of hydrogen peroxide to moles of nitrobenzene.

Organic base, particularly tetramethylammonium hydroxide, may be recycled from the products of the reduction reaction, alone or with make-up quantities of fresh base or purified recycle base or both, for use in the reaction of said method. The hydrogen peroxide may then be supplied as an aqueous solution comprising from about 20 wt. % to about 40 wt. % in an amount of from about 0.01 to about 0.25 moles of hydrogen peroxide to moles of nitrobenzene, or more preferred, wherein the hydrogen peroxide is provided in an amount of from about 0.06 to about 0.21 moles of hydrogen peroxide to moles of nitrobenzene, or, still more preferred, wherein the hydrogen peroxide is supplied in an amount of from about 0.08 to about 0.17 moles of hydrogen peroxide to moles of nitrobenzene. The hydrogen peroxide may be supplied as an aqueous solution comprising from about 3 wt. % to about 7 wt. % in an amount of from about 0.01 to about 0.20 moles of hydrogen peroxide to moles of nitrobenzene, preferably from about 0.03 to about 0.16 moles of hydrogen peroxide to moles of nitrobenzene or, still more preferred, wherein the hydrogen peroxide is supplied in an amount of from about 0.06 to about 0.12 moles of hydrogen peroxide to moles of nitrobenzene. Similar effective mole ratio ranges can be defined by one skilled in the art for other concentrations of hydrogen peroxide in the range of 3 wt. % to 50 wt. %. It is also possible to get an equivalent selectivity with less hydrogen peroxide for any peroxide concentration included herein by feeding the peroxide for only part of the time that nitrobenzene is fed, or by varying the rate at which peroxide is fed, or both.

Purified recycle base may be used as the sole base or with make-up quantities of fresh base and the nitrobenzene feed time may be about 100 minutes or less.

The reactive contact in the coupling reaction in the method of the invention may be carried out at a temperature of from about 20° C. to about 125° C., preferably from about 65° C. to about 90° C. Other conditions for the reactive contact include pressures in the range of from about 20 mbar to about atmospheric. Reaction time is typically less than about 4 hours. It is advantageous to agitate the reaction mixture during the entire reaction.

The invention is illustrated by the following non-limiting examples.

Analytical

Yields of individual components were determined by external standard HPLC, from the average of duplicate analyses. Approximately 0.06 grams of material to be analyzed is accurately weighed into a 50-mL volumetric flask and diluted with a buffer solution containing 39% v/v water, 36% v/v acetonitrile, 24% v/v methanol and 1% v/v pH 7 buffer. The solution is injected through a 10 µL loop onto a reversed phase Zorbax ODS HPLC column (250×4.6 mm) using a binary gradient pumping system and the following elution gradient at a constant flow rate of 1.5 mL/minute:

| Time, minutes | % Eluant A | % Eluant B |
|---|---|---|
| 0 | 100 | 0 |
| 25 | 25 | 75 |
| 35 | 0 | 100 |
| 37.5 | 0 | 100 |
| 38 | 100 | 0 |
| 40 | 100 | 0 |

Eluant A is 75% v/v water, 15% v/v acetonitrile and 10% v/v methanol. Eluant B is 60% v/v acetonitrile and 40% v/v methanol. Detection is UV at 254 nm.

Experimental

Experimental procedures are described within each example. Experiments with recycle base used typical samples from a commercial plant operating without peroxide addition, for which TMAH assay (24.4 wt. % and 26.8 wt. %) was determined by titration. The recycle base contained various tetramethylammonium salts plus aniline and low levels of other organic impurities. One of the salts is $(TMA)_2CO_3$, which contributes to the assay for recycle base, as the first equivalent titrates along with TMAH.

Conversion for the examples was calculated based on the amount of unreacted nitrobenzene remaining in the final coupling reaction mass. Conversion was assumed to be 100% if no nitrobenzene was detected. Selectivity is defined by the following molar ratio: (p-NDPA+4-NDPA)/(p-NDPA+4-NDPA+azobenzene+phenazine). 4-NDPA is 4-nitrodiphenylamine and p-NDPA is 4-nitrosodiphenylamine. In the examples, "NB" is nitrobenzene, "t-Azo" is transazobenzene, "Phen" is phenazine, and "Other" refers to aniline and nitrobenzene coupling by-products, mostly 4-phenylazodiphenylamine, and any unknowns.

EXAMPLE 1

This example provides reference information, for discussion of the effect of using hydrogen peroxide during the coupling reaction in the other examples. The procedure for Runs 1-3 is similar to that of Example 2, except using plant recycle TMAH (26.8 wt. %) and plant recycle aniline, with base concentration and drying at 62 torr and reaction at 60 torr. The procedure for Runs 4-6 is to charge 145.28 g of fresh aniline (1.56 moles) and 87.36 g of aqueous pre-concentrated fresh TMAH solution (36.0 wt. %, 0.345 moles TMAH) to a 500-mL round bottom flask equipped with a thermocouple, heating mantle, subsurface feed tubes for nitrobenzene and peroxide or water and a Teflon paddle stirrer. With pressure at 70 torr, the mixture is heated to remove 18 mL of water, along with aniline, (~30 minutes) and then nitrobenzene feed (36.93 g, 0.30 moles) is started. Temperature rises from about 66-67° C. to 80° C. during the reaction period, while water and aniline are boiled off. Table 1 gives the times for nitrobenzene feed and reaction hold for all six runs. Water and aniline are boiled off during the hold. Batches for Runs 4-6 are quenched with 20 mL of water after the hold period. The hydrogen peroxide charge is 20.40 g (0.03 moles) of a 5 wt. % aqueous solution concurrent with nitrobenzene. Since water can affect selectivity by protecting TMAH from degradation and by shifting reaction equilibriums, water is fed concurrently with nitrobenzene for direct comparison with peroxide.

The example illustrates that both shorter nitrobenzene feed time and the addition of water can increase selectivity, although water is not very effective for the longer feed time. However, peroxide gave the highest selectivity, 1.9% greater than water addition. More importantly, for a commercial process that involves recycles and waste disposal, aqueous peroxide greatly reduced the levels of two key by-products compared to water alone, viz. azobenzene (by 39%) and phenazine (by 36%). Replicate baseline runs by a slightly different procedure gave selectivities of 92.7% and 92.6%, indicating that the experimental results reported herein are very reproducible. Moreover, the replicates indicate that the small selectivity differences, such as 1.9% higher for peroxide vs. water, are indeed significant.

TABLE 1

Background Data for Hydrogen Peroxide Comparison

| | Time (m) | | Conv | Selec | Batch Product Composition (wt. %) | | | |
|---|---|---|---|---|---|---|---|---|
| Additive | Feed | Hold | (%) | (%) | p-NDPA | 4-NDPA | t-Azo | Phen |
| 1. None | 110 | 20 | ~99 | 91.5 | 25.36 | 2.30 | 2.01 | 0.32 |
| 2. Water[1] | 110 | 20 | ~99 | 91.9 | 26.24 | 2.30 | 2.01 | 0.29 |
| 3. Water[2] | 110 | 20 | ~98 | 91.5 | 25.91 | 2.45 | 2.14 | 0.25 |
| 4. None | 80 | 40 | 100.0 | 94.0 | 26.61 | 2.32 | 1.31 | 0.37 |
| 5. Water[3] | 80 | 40 | 100.0 | 95.3 | 30.11 | 2.02 | 1.04 | 0.39 |
| 6. Peroxide[4] | 80 | 40 | 100.0 | 97.2 | 31.42 | 2.42 | 0.63 | 0.25 |

[1]$H_2O/NB$ = 0.56 molar;
[2]$H_2O/NB$ = 1.9 molar; average of two batches
[3]Water charge weight equal to 5 wt. % peroxide charge weight, $H_2O/NB$ = 3.8 molar
[4]5.0 wt. % hydrogen peroxide aqueous solution at $H_2O_2/NB$ = 0.10

EXAMPLE 2

Some of the runs in the following examples had relatively low conversions, because the procedure used a fixed nitrobenzene feed time plus hold time rather than holding the batches to reaction completion. This example shows the effect of an extended hold period on selectivity.

The procedure is to charge 432.85 g of plant recycle base (24.4 wt. % TMAH, 1.6 moles) to a 1. L water/glycol jacketed reactor. Begin agitation at 150 rpm and boil off 92 mL water at constant pressure of 65 torr, with the water bath temperature starting at 72° C. and increasing by 1° C. per 10 mL of water removed. Then charge 301.50 g (3.24 moles) of fresh aniline via vacuum. Continue to remove water plus aniline at 65 torr, by raising the bath temperature 1° C. per 9 mL of water removed, while continuously charging 120 mL of aniline from a sidearm pressure-vented dropping funnel. When 72 mL of water has been removed (164 mL total), begin co-feeding 123.11 g of nitrobenzene (1.00 moles) and 27.20 g hydrogen peroxide (10 wt. % aqueous solution, 0.08 moles) subsurface via peristaltic pumps over a period of 80 minutes. Continuously add 60 mL of aniline during the reaction step, while holding pressure at 65 torr and boiling off water plus aniline. Gradually increase bath temperature in 0.5° C. increments to achieve 91° C. in the bath and 80-82° C. in the reactor by the end of the reaction step. Initiate the hold period by reducing pressure to 60 torr and increasing the bath and reactor temperatures by another 1° C. Continue removing water plus aniline during an extended hold.

This example shows that holding a low conversion batch to essentially complete conversion had only a minimum impact on selectivity. In the examples following this one, conversion ranged from 73.4% to 100%. These results show that driving conversion from 89.3% to 99.8% reduced selectivity by only 0.5% and going from 96% to 99.8% conversion reduced selectivity by only 0.2%. Therefore, low conversion for some runs in the following examples does not affect the conclusions.

TABLE 2

Peroxide Batch Profile of Extended Hold

| Hold Time (minutes) | Conv (%) | Selec (%) | Batch Product Composition (wt. %) | | | |
|---|---|---|---|---|---|---|
| | | | p-NDPA | 4-NDPA | t-Azo | Phen |
| 0 | 89.3 | 97.5 | 22.78 | 1.50 | 0.36 | 0.20 |
| 10 | 93.9 | 97.2 | 24.37 | 1.72 | 0.49 | 0.21 |
| 20 | 95.9 | 97.2 | 25.00 | 1.82 | 0.49 | 0.20 |
| 30 | 97.1 | 97.1 | 25.05 | 1.86 | 0.51 | 0.22 |
| 40 | 97.9 | 97.1 | 25.45 | 1.91 | 0.53 | 0.21 |
| 50 | 98.5 | 97.1 | 25.70 | 1.95 | 0.53 | 0.21 |
| 60 | 98.9 | 97.1 | 26.07 | 2.00 | 0.55 | 0.22 |
| 70 | 99.2 | 97.1 | 26.22 | 2.01 | 0.56 | 0.22 |
| 80 | 99.5 | 97.1 | 26.48 | 2.04 | 0.57 | 0.22 |
| 90 | 99.7 | 97.0 | 26.59 | 2.06 | 0.58 | 0.22 |
| 100 | 99.8 | 97.0 | 26.83 | 2.09 | 0.61 | 0.22 |

EXAMPLE 3

A 3-factor, 8-run Design of Experiments (DOE) with pressure, nitrobenzene feed rate, and peroxide as variables was executed. Concentration of peroxide (5 wt. % aqueous solution) and $H_2O_2$/NB (0.1 molar ratio) were arbitrarily selected for the four runs using peroxide. To a 500-mL round bottom flask equipped with a eating mantle, thermocouple, subsurface feed tubes for nitrobenzene and peroxide and a Teflon paddle stirrer was charged 130.02 g of recycle base (24.4 wt. %), which was then concentrated to 31 wt. % by boiling off 28 mL of water at the pressure indicated in Table 3. Then 145.28 g of aniline was added and another 16 mL of water was removed, along with aniline (44 mL total water). Then nitrobenzene feed of 36.93 g was started, with continued boil off of water and aniline. When peroxide was used, the 20.40 g of 5 wt. % peroxide solution was co-fed with nitrobenzene at an appropriate feed rate to finish with nitrobenzene. Batches were held as described below, then quenched with 20 mL of water. Reactions were run at 80° C. and either 65 or 95 torr (specified in the design) on a 0.3 mole scale. Hold periods were fixed at 20 minutes for the 110 minute nitrobenzene feed and 45 minutes for the 70 minute nitrobenzene feed, both with continued boil off of water and aniline.

Results in Table 3 show that selectivity is consistently higher when peroxide is used at a low level and the range is much smaller (96.1 to 96.6% with vs. 89.8 to 94.8% without) for variations of reaction pressure and nitrobenzene feed rate. Also, with peroxide more 4-NDPA was made relative to azobenzene, whereas without, nearly equimolar amounts were generated. Less 4-NDPA (by 30-40%) was made with peroxide at the longer nitrobenzene feed time and in all runs, much less azobenzene and phenazine were made with peroxide. Example 1 showed that nitrobenzene feed rate can affect selectivity without peroxide and this example shows that peroxide reduces the effect of both nitrobenzene feed rate and reaction pressure, which is unexpected.

TABLE 3

Three Factor Experimental Design for Peroxide

| | Run Nr. | | | | | | | |
|---|---|---|---|---|---|---|---|---|
| | 1 | 2 | 3 | 4 | 5 | 6 | 7 | 8 |
| Design Targets | | | | | | | | |
| NB Feed Rate (m) | 75 | 75 | 110 | 110 | 75 | 75 | 110 | 110 |
| Pressure (torr) | 95 | 65 | 95 | 65 | 95 | 65 | 95 | 65 |
| Peroxide | Yes | Yes | Yes | Yes | No | No | No | No |
| Actual NB Feed (m) | 74 | 76 | 113 | 111 | 73 | 74 | 115 | 112 |
| Results | | | | | | | | |
| Conversion (%) | 98.1 | 99.8 | 89.6 | 96.8 | 99.7 | 100.0 | 98.9 | 100.0 |
| Selectivity (%) | 96.1 | 96.4 | 96.6 | 96.5 | 94.8 | 92.8 | 94.5 | 89.8 |
| Batch Product Composition (wt. %) | | | | | | | | |
| p-NDPA | 24.05 | 26.06 | 22.76 | 24.31 | 24.31 | 24.23 | 23.78 | 22.35 |
| 4-NDPA | 1.78 | 2.13 | 1.20 | 1.83 | 1.66 | 2.21 | 1.71 | 2.98 |
| t-Azobenzene | 0.85 | 0.77 | 0.62 | 0.68 | 1.09 | 1.58 | 1.11 | 2.28 |
| Phenazine | 0.12 | 0.18 | 0.14 | 0.20 | 0.21 | 0.30 | 0.25 | 0.34 |

EXAMPLE 4

A refining DOE was completed to assess both 1) amount of peroxide and 2) peroxide concentration for the coupling reaction. The procedure was the same as for Example 3, except for the mole ratios and peroxide concentrations listed in Table 4 and a nitrobenzene feed time of about 70 minutes with a 30 minute hold. Table 4 shows that with a fast nitrobenzene feed rate, selectivity is relatively independent of peroxide concentration, especially at the lower molar ratio. This is surprising, because Example 1 showed that adding water can increase selectivity and the runs with 5 wt. % peroxide had 6.33 times the amount of water as 25 wt. % peroxide. The results also show that selectivity can be affected by the amount of oxidant. A comparison of Runs with equal peroxide concentration in Table 4 shows that the higher mole ratio gave lower selectivity in each case. Again, this is surprising, since twice the amount of water was added at the higher mole ratio. So the benefits of water and peroxide are not additive, as the effect of peroxide predominates.

TABLE 4

Refining Design of Experiments

| | Run Nr. | | | |
|---|---|---|---|---|
| | 1 | 2 | 3 | 4 |
| Design Targets | | | | |
| $H_2O_2$:NB, molar | 0.10 | 0.10 | 0.20 | 0.20 |
| Peroxide Concentration | 5 wt. % | 25 wt. % | 5 wt. % | 25 wt. % |
| NB Feed Time (m) | 68 | 72 | 70 | 70 |
| Relative Water Charge | 6.33 | 1.0 | 12.7 | 2.0 |
| Results | | | | |
| Conversion (%) | 98.1 | 98.3 | 98.6 | 97.8 |
| Selectivity (%) | 96.4 | 96.0 | 92.8 | 93.8 |
| Batch Product Composition (wt. %) | | | | |
| p-NDPA | 25.62 | 24.41 | 27.86 | 25.40 |
| 4-NDPA | 2.06 | 2.08 | 2.84 | 2.45 |
| t-Azobenzene | 0.80 | 0.79 | 2.05 | 1.53 |
| Phenazine | 0.14 | 0.21 | 0.13 | 0.16 |

EXAMPLE 5

This example further illustrates the effect of pressure on selectivity when peroxide is used. The batches were made by a procedure similar to Example 2, with a nitrobenzene feed time of 110 minutes, a hold time of 20 minutes, a different sample of plant recycle base (26.8 wt. %) and plant recycle aniline instead of fresh. The results in Table 5 show that pressure does not have an impact on selectivity when 30 wt. % peroxide is used, just as in Example 3 with 5 wt. % peroxide. This is additional evidence that peroxide mitigates the effect of other reaction variables.

TABLE 5

Effect of Reaction Pressure with Peroxide

| | Pressure, mbara | |
|---|---|---|
| | 80 | 160 |
| Selectivity (%) | 95.56 | 95.52 |

EXAMPLE 6

Example 1 showed that shorter nitrobenzene feed time (80 minutes) alone, or with water, or with aqueous peroxide, can increase selectivity. Example 3 showed that for a fixed peroxide concentration and molar ratio, nitrobenzene feed time (about 75 minutes vs. about 110 minutes) had little effect on selectivity. Example 4 showed that with a short nitrobenzene feed time (about 70 minutes), selectivity is relatively independent of peroxide concentration, especially at the lower mole ratio.

This example explores the effect of peroxide concentration on selectivity for a longer nitrobenzene feed time. A series of batches were made by a procedure similar to that of Example 5. Also, peroxide feed for the 0.064 mole ratio runs was via a piston pump (see Example 14). Peroxide concentration was varied from 5 wt. % to 35 wt. %, with $H_2O_2$/NB=0.1 and 0.064. The results in Table 6 show that also for a longer nitrobenzene feed time, selectivity is essentially independent of peroxide concentration. Moreover, phenazine level increases only slightly as significantly less water is charged with the peroxide, which is consistent with Example 4. With a longer nitrobenzene feed time, the rate of removal of water relative to the rate of nitrobenzene charge is greater than for a shorter nitrobenzene feed time. So as less water is charged with the peroxide, the batches become even drier. However, even the lowest water charge in Table 6 has significantly higher selectivity than for water alone with a 110 minute nitrobenzene feed in Table 1. This illustrates that although water and peroxide can both play a role in increasing selectivity, the effect of peroxide is more important. Furthermore, since water can influence the rate of formation of the Meisenheimer complex and the rate of its oxidation by nitrobenzene, it should be possible to improve selectivity with peroxide by tuning $H_2O_2$/NB to match the Meisenheimer concentration in the batch.

TABLE 6

Effect of Peroxide Concentration

| Peroxide, Wt. % | $H_2O_2$/NB Molar | $H_2O$/NB Molar | Selec (%) | Batch Product Composition (wt %) | | | |
|---|---|---|---|---|---|---|---|
| | | | | p-NDPA | 4-NDPA | t-Azo | Phen |
| 0 | 0 | 0 | 91.5 | 25.36 | 2.30 | 2.01 | 0.32 |
| 5 | 0.10 | 3.59 | 96.1 | 27.56 | 2.99 | 0.98 | 0.16 |
| 10 | 0.10 | 1.70 | 96.0 | 26.82 | 3.24 | 0.96 | 0.17 |
| 20 | 0.10 | 0.76 | 95.1 | 27.22 | 2.75 | 1.22 | 0.18 |
| 20 | 0.10 | 0.76 | 95.3 | 26.53 | 3.02 | 1.16 | 0.19 |
| 24.3 | 0.064 | 0.38 | 95.8 | 26.63 | 2.53 | 0.92 | 0.24 |

TABLE 6-continued

Effect of Peroxide Concentration

| Peroxide, Wt. % | $H_2O_2$/NB Molar | $H_2O$/NB Molar | Selec (%) | Batch Product Composition (wt %) | | | |
|---|---|---|---|---|---|---|---|
| | | | | p-NDPA | 4-NDPA | t-Azo | Phen |
| 24.3 | 0.064 | 0.38 | 96.1 | 26.38 | 2.55 | 0.86 | 0.21 |
| 30 | 0.10 | 0.44 | 95.7 | 26.95 | 2.59 | 1.00 | 0.22 |
| 30 | 0.10 | 0.44 | 95.1 | 26.72 | 3.07 | 1.21 | 0.20 |
| 35 | 0.064 | 0.22 | 96.1 | 26.41 | 2.63 | 0.87 | 0.21 |
| 35 | 0.064 | 0.22 | 96.4 | 26.42 | 2.64 | 0.79 | 0.20 |

EXAMPLE 7

A series of coupling reactions were done with a fixed peroxide concentration of 5 wt. % to determine the effect of temperature on selectivity. The procedure was as follows: Charge 130.02 g recycle base (24.4 wt. % TMAH) to 500-mL scale coupler and boil off 28 mL of water. Add 145.28 g aniline and remove another 16 mL of water, along with aniline (44 mL total water). Feed 36.93 g nitrobenzene concurrently with 5 wt. % aqueous peroxide solution at $H_2O_2$/NB=0.08 molar, both subsurface, while boiling off water and aniline. Complete the co-feed in 100-110 minutes at the temperatures indicated in Table 7 and at a constant pressure of 65 torr. Hold for 30 minutes, while boiling off water and aniline, and then quench with 20 mL of water.

The results in Table 7 illustrate the effect that the rates of formation and intramolecular oxidation of the Meisenheimer complex have on selectivity with peroxide. As temperature is increased, selectivity reaches a maximum at about 80° C. At lower temperatures, the rate of Meisenheimer formation is too low for the rate of peroxide addition, so that oxidation of aniline to azobenzene by peroxide increases. At higher temperatures, the higher rate of intramolecular Meisenheimer oxidation to p-NDPA reduces the amount of Meisenheimer available for reaction with peroxide, so that again oxidation of aniline to azobenzene by peroxide increases. Also, the selectivity at 70° C. is higher than that obtained without peroxide at otherwise comparable reaction conditions. Therefore, the effective range for this example can be extended down to about 65° C.

Thus, 80° C. is an apparent optimum that is dependent on the reaction procedure. Any procedure change that will change the rate of Meisenheimer formation, such as changing the rate of water removal, will affect selectivity with peroxide. This could shift the optimum selectivity to a different temperature. Moreover, selectivity can be increased at lower and higher temperatures simply by adjusting the molar ratio of $H_2O_2$/NB to match the rate of formation or rate of intramolecular oxidation of the Meisenheimer. Thus selectivity is highest at 80° C. for this particular reaction procedure with $H_2O_2$/NB=0.08 molar. However, the optimum temperature will vary with other variables, such as water level in the reactor and $H_2O_2$/NB mole ratio. Furthermore, varying temperature will require a different mole ratio of $H_2O_2$/NB for maximum selectivity. Therefore, the effective ranges given in other examples are not absolute.

TABLE 7

Effect of Reaction Temperature with Peroxide

| Temp (° C.) | Conv (%) | Selec (%) | Batch Product Composition (wt. %) | | | | |
|---|---|---|---|---|---|---|---|
| | | | p-NDPA | 4-NDPA | t-Aza | Phen | Others |
| 70 | 73.4 | 94.2 | 16.93 | 1.64 | 0.94 | 0.11 | 0.13 |
| 75 | 93.8 | 96.6 | 24.60 | 1.78 | 0.67 | 0.18 | 0.22 |
| 80 | 97.4 | 97.0 | 26.35 | 1.94 | 0.61 | 0.18 | 0.29 |
| 85 | 99.8 | 95.8 | 26.68 | 2.80 | 0.92 | 0.27 | 0.27 |
| 90 | 100.0 | 89.8 | 25.11 | 4.16 | 2.74 | 0.27 | 0.67 |

EXAMPLE 8

Two sets of coupling reactions were done with fixed peroxide concentrations to determine the effective mole ratio range that would give increased selectivity. The procedure for 5 wt. % peroxide was basically the same as for Example 3. Peroxide and nitrobenzene were fed over 105-110 minutes, with a 20 minute hold period for reaction at 80° C. and 65 torr. The procedure for 30 wt. % was similar to Example 5.

FIG. 1 and Table 8 show that the effective range for 5 wt. % peroxide is about $H_2O_2$/NB=0.01-0.20, the preferred range is about $H_2O_2$/NB=0.03-0.16 and the most preferred range is about $H_2O_2$/NB=0.06-0.12. The optimum molar ratio with 5 wt. % peroxide was $H_2O_2$/NB=0.07-0.09 for this procedure, which is about the same as the mole % of 4-NDPA that was made from nitrobenzene. So peroxide reacts in high selectivity to make 4-NDPA with minimum formation of azobenzene.

This is a surprising result, due to the very large molar excess of aniline that is available to be oxidized to azobenzene. The effective mole ratio range for 30 wt. % peroxide is about 0.01-0.25. An optimum cannot be derived from the data, but it appears to be within 0.06-0.21, which is shifted higher than for 5 wt. % peroxide. A more preferred range appears to be within 0.08-0.17. So the effective mole ratio range, preferred range and most preferred range for peroxide are expected to vary with some process variables, such as peroxide concentration, impurity levels in recycle streams, reaction temperature, water removal rate and nitrobenzene feed rate. Therefore, these ranges are not absolute for peroxide, but rather representative. It is envisaged that the effective range could extend to $H_2O_2$/NB=0.01-0.4 with recycle base or perhaps even somewhat wider.

TABLE 8

Optimization of Peroxide Molar Charge with Recycle Base

| $H_2O_2$ wt. % | $H_2O_2$/NB Molar | Conv (%) | Selec (%) | Batch Product Composition (wt. %) | | | |
|---|---|---|---|---|---|---|---|
| | | | | p-NDPA | 4-NDPA | t-Azo | Phen |
| 5 | 0.00 | 100.0 | 91.7 | 23.78 | 2.76 | 1.84 | 0.35 |
| | 0.04 | 99.2 | 93.7 | 24.16 | 2.39 | 1.31 | 0.33 |
| | 0.06 | 98.9 | 96.0 | 25.14 | 2.36 | 0.75 | 0.29 |
| | 0.07 | 98.0 | 96.9 | 25.22 | 1.95 | 0.55 | 0.24 |
| | 0.08 | 98.3 | 96.9 | 25.66 | 2.04 | 0.57 | 0.23 |
| | 0.09 | 97.6 | 96.9 | 25.46 | 1.94 | 0.59 | 0.20 |
| | 0.10 | 97.6 | 96.7 | 25.80 | 1.97 | 0.68 | 0.19 |
| | 0.12 | 98.3 | 96.0 | 26.02 | 2.15 | 0.91 | 0.17 |
| | 0.16 | 97.5 | 93.9 | 25.05 | 2.11 | 1.42 | 0.20 |
| | 0.20 | 97.0 | 92.2 | 25.19 | 2.27 | 1.97 | 0.16 |
| 30 | 0.00 | ~99.0 | 91.5 | 25.36 | 2.30 | 2.01 | 0.32 |
| | 0.05 | ~98.5 | 92.1 | 26.00 | 3.08 | 2.04 | 0.23 |
| | 0.10 | ~96.5 | 95.7 | 26.95 | 2.59 | 1.00 | 0.22 |
| | 0.10 | ~97.0 | 95.1 | 26.72 | 3.07 | 1.21 | 0.20 |
| | 0.20 | ~94.5 | 92.7 | 25.94 | 3.04 | 1.92 | 0.16 |

EXAMPLE 9

Figure 2:
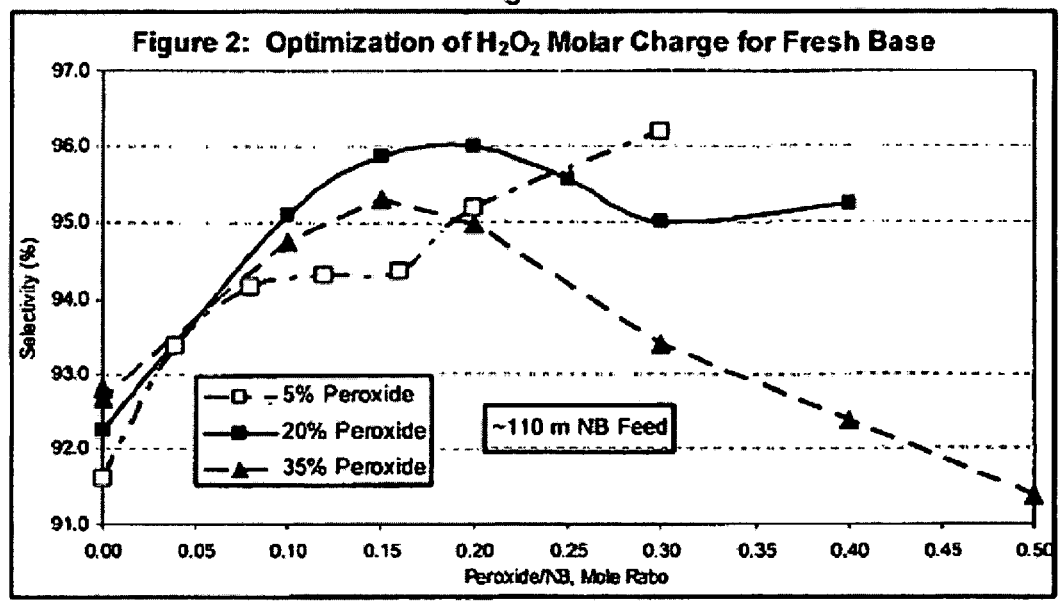
FIG. 2 is a graph showing the optimization $H_2O_2$ molar charge for fresh base based on Example 9.

An optimization study was done for fresh base with peroxide to examine the effect of base quality. The procedure was similar to Example 3 for 5 and 20 wt. %, with a 126.89 g charge of 25 wt. % base, and to Example 10 for 35 wt. %. As seen in FIG. 2 and Table 9, fresh base gave flatter and wider optimization curves vs. recycle base. Moreover, the optimum mole ratio and effective range varied with concentration, the maximum selectivity was lower vs. recycle base and selectivity increased after the initial optimum was passed. The upturns are due to the higher water charge as mole ratio increased, which did not occur with 35 wt. % peroxide, for which the least water was added. Selectivity rose because water inhibits oxidation of Meisenheimer by nitrobenzene, so that more is oxidized by peroxide. The results show that at the conditions used for Examples 8 and 9, peroxide is more effective with recycle base. Moreover, the salts in recycle base must moderate the effect of water, since the selectivity upturn did not occur with it. Even so, the selectivity increase with fresh base is substantial. The effective range for 35 wt. % peroxide is about 0.01-0.33 and if water was removed faster with 20 wt. % peroxide, the curve tracks to an effective range of about 0.01-0.46. Since nitrobenzene feed rate can extend well beyond 110 minutes for a commercial process, the effective range could well extend to 0.01-0.5 or even somewhat wider. As discussed above, increasing nitrobenzene feed rate gives wetter batches with fresh base, which increases selectivity and should give sharper optimization curves. Thus, the effective range will vary with such variables as nitrobenzene feed rate and water removal rate, but an effective range of about 0.01-0.6 should cover all possibilities. The results with fresh base should also apply to recycle base that has been recovered by electrolysis, such as described in WO 2002034372, or by any other procedure.

TABLE 9

Optimization of Peroxide Molar Charge with Fresh Base

| Peroxide Strength | $H_2O_2$/NB Molar | CONV % | SELEC % | Batch Composition (wt. %) | | | | | |
|---|---|---|---|---|---|---|---|---|---|
| | | | | An | NB | 4-NO | 4-N | t-Azo | Phen |
| 5 wt. % | 0.00 | 100.0 | 91.6 | 44.7 | 0.00 | 25.1 | 2.10 | 1.85 | 0.42 |
| | 0.04 | 100.0 | 93.4 | 43.2 | 0.01 | 26.6 | 2.08 | 1.45 | 0.41 |
| | 0.08 | 100.0 | 94.2 | 41.4 | 0.00 | 26.7 | 1.92 | 1.27 | 0.35 |
| | 0.12 | 100.0 | 94.3 | 41.8 | 0.00 | 27.0 | 2.11 | 1.24 | 0.36 |
| | 0.16 | 100.0 | 94.4 | 39.7 | 0.00 | 27.6 | 2.37 | 1.28 | 0.35 |
| | 0.20 | 100.0 | 95.2 | 38.3 | 0.00 | 28.4 | 2.29 | 1.21 | 0.20 |
| | 0.30 | 99.9 | 96.2 | 37.6 | 0.00 | 27.1 | 2.63 | 0.88 | 0.19 |
| 20 wt. % | 0.00 | 100.0 | 92.2 | 46.8 | 0.00 | 25.4 | 1.88 | 1.69 | 0.40 |
| | 0.10 | 100.0 | 95.1 | 45.7 | 0.00 | 25.6 | 2.10 | 0.94 | 0.36 |
| | 0.15 | 100.0 | 95.9 | 45.6 | 0.00 | 26.6 | 2.20 | 0.85 | 0.28 |
| | 0.20 | 99.9 | 96.0 | 44.2 | 0.02 | 27.0 | 2.13 | 0.84 | 0.27 |
| | 0.25 | 100.0 | 95.6 | 42.6 | 0.00 | 27.5 | 2.55 | 1.05 | 0.22 |
| | 0.30 | 100.0 | 95.0 | 43.2 | 0.00 | 27.1 | 2.62 | 1.20 | 0.22 |
| | 0.40 | 98.9 | 95.2 | 43.0 | 0.20 | 26.1 | 2.56 | 1.11 | 0.20 |
| 35 wt. % | 0.00 | 100.0 | 92.8 | 46.7 | 0.00 | 25.5 | 1.73 | 1.55 | 0.38 |
| | 0.00 | 100.0 | 92.7 | 46.5 | 0.00 | 25.4 | 1.95 | 1.56 | 0.41 |
| | 0.10 | 100.0 | 94.8 | 45.6 | 0.00 | 25.8 | 2.02 | 1.05 | 0.35 |
| | 0.15 | 100.0 | 95.3 | 45.4 | 0.00 | 26.6 | 1.95 | 1.00 | 0.28 |
| | 0.20 | 99.9 | 95.0 | 44.9 | 0.02 | 26.4 | 2.07 | 1.11 | 0.26 |
| | 0.30 | 100.0 | 93.4 | 43.9 | 0.00 | 26.4 | 2.43 | 1.63 | 0.23 |
| | 0.40 | 99.6 | 92.4 | 43.2 | 0.08 | 26.0 | 2.56 | 1.95 | 0.20 |
| | 0.50 | 98.8 | 91.4 | 41.8 | 0.21 | 25.8 | 2.67 | 1.28 | 0.17 |

EXAMPLE 10

This example further illustrates the effect of nitrobenzene feed time and base quality on selectivity. The procedure was similar to Example 3, except that for fresh base, 87.36 g of pre-concentrated base (36 wt. %) was used and water removal after aniline addition was only 18 mL. All batches had $H_2O_2$/NB=0.1 molar ratio. The results in Table 10 show that without peroxide, fresh base gave higher selectivity than recycle base, regardless of nitrobenzene feed time. However, the situation changed significantly when peroxide was used. With peroxide, recycle base gave higher selectivity than fresh base for the longer nitrobenzene feed time, but equivalent selectivity for the shorter feed time.

These results can be partially explained by the effect of nitrobenzene feed time and base quality on water level in the batch. For example, the salts dissolved in recycle base elevate the boiling point, so that at constant reaction temperature and pressure, recycle base batches will be wetter than fresh base batches. However, fresh base has a higher concentration of TMAH, as determined by titration, than recycle base. Recycle base contains $TMA_2CO_3$ as the largest impurity and the first equivalent of $TMA_2CO_3$ titrates as TMAH. For example, 25 wt. % recycle base with 10 wt. % $TMA_2CO_3$ is actually only 20.6 wt. % TMAH. Since $TMA_2CO_3$ is a less effective base for the coupling reaction than TMAH, fresh base gives better reactivity. Without peroxide, the better reactivity explains the higher selectivity with fresh base in spite of the drier conditions. So with peroxide, equivalent to higher selectivity for recycle base is surprising, especially since the actual recycle base that was used was only 24.4 wt. % assay by titration. Peroxide is able to overcome the inefficiency due to low TMAH level and salts dissolved in recycle base.

water amount added with 5 wt. % vs. 30 wt. % peroxide. Since water added had little effect at constant peroxide addition, this indicates that peroxide addition has a greater influence than water addition. This is additional evidence that peroxide has modified the coupling reaction system to minimize side reactions.

EXAMPLE 12

This example illustrates that a partial feed of peroxide can increase the efficiency of the peroxide. The equipment is the same as for Example 2 and the basic procedure is similar. Charge 432.85 g of 24.4 wt. % recycle base, begin agitation at 150 rpm and then heat to boil off 92 mL of water at 65 torr. Add 301.50 g of aniline and boil off water plus aniline at 65 torr, while continuing to add more aniline. When 164 mL of water plus aniline has been removed, begin to feed 123.11 g of nitrobenzene over the time indicated in Table 11, while continuing to add more aniline and boil off water plus aniline. The aniline charge during drying plus reaction is 180.90 g. Aqueous peroxide solution is fed concurrently with nitrobenzene over the times indicated in Table 11. Reaction conditions are 80° C. and 65 torr. After the completion of nitrobenzene feed, hold at 60 torr for 30 minutes and then quench with 50 mL of water.

Runs 1 and 2 in Table 11 show that it is possible to obtain somewhat higher selectivity when peroxide is fed for only part of the nitrobenzene feed time. The benefits from this could either be the increased selectivity, or reduced peroxide charge (and hence cost) for the same selectivity. For example, Runs 3 and 4 show only a small drop in selectivity (0.37%) for a 25% reduction in the peroxide charge from the use of partial feed.

TABLE 10

Effect of Peroxide with Variable Base Quality

| | Pressure, torr | | | | |
|---|---|---|---|---|---|
| | 95 | 65-70 | 65 | 65-70 | 65-70 |
| NB Feed Time Target (m) | 75-80 | 75-80 | 105-110 | 75-80 | 110-130 |
| Peroxide (5 wt. %) | Yes | Yes | Yes | No | No |
| Base Quality | | | Selectivity (%) | | |
| Recycle | 96.1 | 96.4 | 96.5 | 92.8 | 89.8 |
| Fresh | 96.4 | 97.2 | 94.2 * | 94.0 | 91.8 |

* Average of 0.08 & 0.12 mole ratios from Table 9; started with 25 wt. % TMAH

EXAMPLE 11

Figure 3:
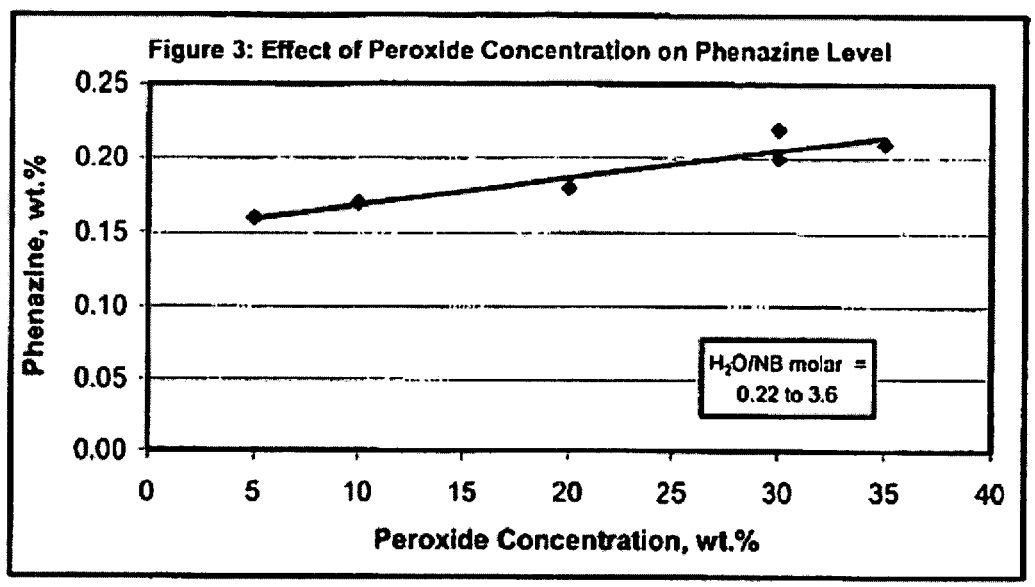
FIG. 3 is a graph showing the effect of peroxide concentration on phenazine level based on data from Example 6.
Figure 4:
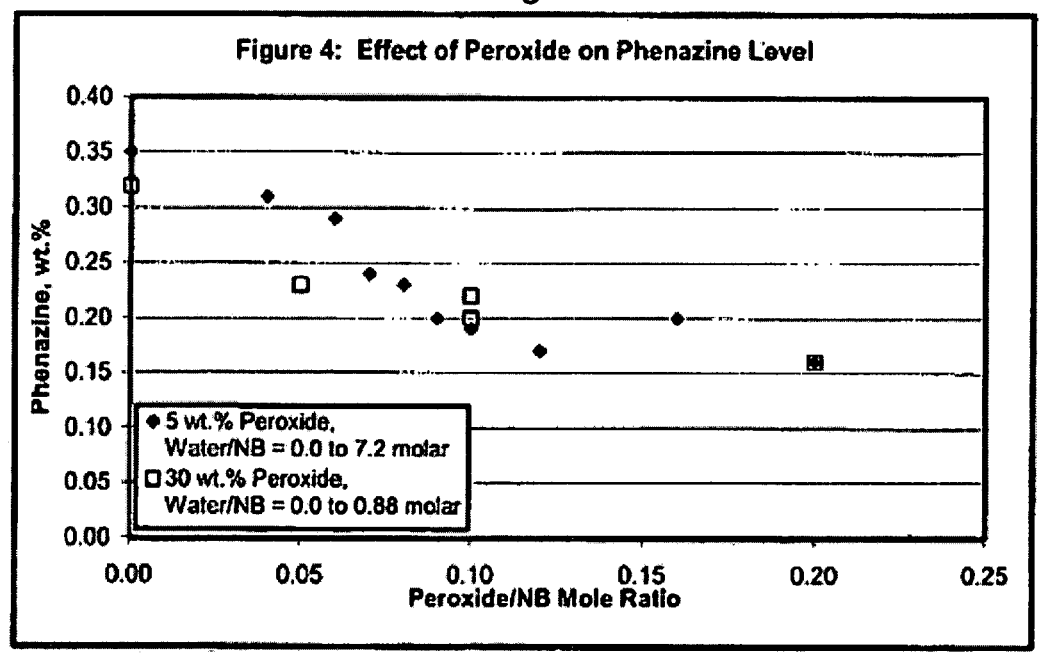
FIG. 4 is a graph showing the effect of peroxide concentration on phenazine level based on data from Example 8.

It has been reported in U.S. Pat. No. 5,117,063, incorporated herein by reference, and related patents that the amount of water present during the coupling reaction has a profound effect on the molar ratio of (p-NDPA+4-NDPA)/(2-NDPA+ Phenazine). Data in Example 4 indicated that water added with peroxide has minor impact on the amount of phenazine that is made (2-NDPA is not observed to form at all). This is further illustrated in the FIGS. 3 and 4. Data in FIG. 3 (from Example 6) show that phenazine level increased only slightly for a seven-fold increase in peroxide concentration, despite the 16-fold decrease in water amount of water added with the peroxide. Data in FIG. 4 (from Example 8) show that phenazine level decreased significantly as the $H_2O_2$/NB mole ratio increased. However, phenazine level was essentially independent of peroxide concentration, despite an eight-fold higher

TABLE 11

Comparison of Full and Partial Peroxide Feed

| | Run Number | | | |
|---|---|---|---|---|
| | 1 | 2 | 3 | 4 |
| $H_2O_2$ Feed Profile | Full | Partial | Partial | Full |
| $H_2O_2$ Feed, % of NB Feed Time | 99 | 61 | 78 | 100 |
| $H_2O_2$ Concentration, wt. % | 15.0 | 15.0 | 22.5 | 22.5* |
| $H_2O_2$/NB mole ratio, Overall | 0.04 | 0.04 | 0.06 | 0.08 |
| $H_2O_2$/NB mole ratio, during Feed | 0.04 | 0.066 | 0.077 | 0.08 |
| NB Feed Time, minutes | 107 | 109 | 110 | 107 |
| $H_2O_2$ Feed Start, minutes | 0 | 21 | 11 | 0 |
| $H_2O_2$ Feed End, minutes | 106 | 87 | 97 | 107 |

TABLE 11-continued

Comparison of Full and Partial Peroxide Feed

| | Run Number | | | |
|---|---|---|---|---|
| | 1 | 2 | 3 | 4 |
| Conversion, % | 99.12 | 98.71 | 97.80 | 97.55 |
| Selectivity, % | 94.12 | 94.74 | 96.33 | 96.70 |

*Average of virtually identical results for 15% and 30% peroxide; this is consistent with Example 5, which shows flat results for 20 to 30% peroxide.

EXAMPLE 13

This example compares the effect of base quality with partial feed of the peroxide. Equipment is the same as for Example 2 and the basic procedure is similar. The main difference is that the start of peroxide feed was delayed by about 5 minutes and ended about 10 minutes ahead of the nitrobenzene feed time, which was a target of 105 minutes. Peroxide was charged as an aqueous 24.3 wt. % solution, with $H_2O_2$/NB=0.064 molar. The results in Table 12 indicate that under the conditions of the experiment, plant recycle base, fresh base and base recovered by electrolysis from plant recycle base give equivalent results. This demonstrates that recovered base is suitable for use with peroxide, either alone or in combination with recycle and/or fresh base. It also further demonstrates that peroxide overcomes the advantage that fresh base has without peroxide.

TABLE 12

Comparison of Base Types

| Base Type | Base Assay (wt. %) | Selectivity (%) |
|---|---|---|
| Plant Recycle | 24.4 | 96.04 |
| Fresh | 25.0 | 96.20 |
| Recovered by Electrolysis | 20.2 | 96.16 |

EXAMPLE 14

This example illustrates that good contact of peroxide with the Meisenheimer complex is essential for optimum selectivity. Table 13 compares feeding peroxide in the lab via a peristaltic pump vs. a piston pump that delivers peroxide in 20 µL increments. The procedure was similar to that of Example 2, except that for the lower mole ratio runs, peroxide feed was started 5 minutes later and was completed 10 minutes earlier than nitrobenzene. The data in Table 13 show that the peristaltic pump gave erratic and lower selectivity than the piston pump. Example 12 shows that the comparison of the two mole ratios with partial vs. full feed is valid. The small volumetric inputs of the piston pump ensures that the peroxide is quickly dispersed for intimate contact with the Meisenheimer. The larger slugs of peroxide input from the peristaltic pump gave worse dispersion, which reduced the efficiency of peroxide interaction, resulting in lower selectivity. Good dispersion is especially important at higher peroxide concentrations, because of the localized higher mole ratio of peroxide (in a drop of peroxide) to reaction mass. This supports the need to introduce peroxide at the point of highest Meisenheimer concentration.

TABLE 13

Comparison of Peroxide Pumps for Dispersion

| $H_2O_2$ Pump | Nr. of Runs | $H_2O_2$ Conc. (wt. %) | $H_2O_2$/NB, molar | Selectivity (%) |
|---|---|---|---|---|
| Peristaltic | 1 | 24.3 | 0.064 | 96.05 |
| Piston | 2 | 24.3 | 0.064 | 95.82-96.09 |
| Peristaltic | 3 | 35.0 | 0.10 | 93.61-94.36 |
| Piston | 2 | 35.0 | 0.064 | 96.07-96.39 |

EXAMPLE 15

This example demonstrates the suitability of aqueous 50 wt. % hydrogen peroxide for the coupling of aniline with nitrobenzene in the presence of a strong organic base. The procedure of Example 13 was followed, except that aqueous 50 wt. % hydrogen peroxide was used. The peroxide solution was carefully fed subsurface into the reactor by hand control of the peristaltic pump to give as smooth an addition as possible, considering the small amount of material to charge (4.35 g). A selectivity of 95.56% was obtained, which is only slightly lower than selectivities with lower peroxide concentrations. The results of Example 14 show that if a small piston pump had been available for this experiment, 50 wt. % peroxide would most likely have given selectivity identical to the lower concentrations. The conclusion in any case is that 50 wt. % is a suitable concentration for hydrogen peroxide.

COMPARATIVE EXAMPLE 1

This example demonstrates that hydrogen peroxide is superior to air as an oxidant for the coupling of aniline with nitrobenzene in the presence of a strong organic base. Several coupling batches were made by a procedure similar to that of Example 1, wherein air was used as the oxidant at various flow rates. The results in Table 14 show that air is impractical as an oxidant, as flow rates required for a significant increase in selectivity would overload a typical plant condenser.

Moreover, the highest selectivity obtained is well below the selectivities obtained with peroxide over a range of conditions.

TABLE 14

Effect of Air on Selectivity

Air Flow, Based on 700 g Total Mass in 1-L Scale Lab Batch

| Air Inlet | Lab Flow (mL/min) | Plant Equivalent ($Nm^3$/hr) | Selectivity (%) |
|---|---|---|---|
| No Air (3 batches) | 0.0 | 0.0 | 93.0-93.1 |
| Subsurface | 2.6 | 20 | 93.1 |
| Subsurface | 14.2 | 110 | 93.5 |
| Head Space | 14.2 | 110 | 93.9 |
| Subsurface | 58.4 | 450 | 94.0 |
| Typical Condenser Design Flow Rate: | | 18 | |

COMPARATIVE EXAMPLE 2

This example examines the effect of peroxide with a strong inorganic base and phase transfer catalyst (PTC), by the following procedure. Aniline (99%, 22.58 g, 240 mmoles), nitrobenzene (99%, 4.97 g, 40 mmoles), hydrogen peroxide (50 wt. % aqueous, molar amount indicated below in FIG. 5), water (water is added such that the total water is kept constant at 2.16 g), potassium hydroxide (86% ground powder, 7.83 g, 120 mmoles) and tetramethylammonium chloride (97%, 4.52 g, 40 mmoles) was charged to a 50-mL round bottom flask equipped with a magnetic stirrer. Peroxide was charged to the reaction mixture before adding KOH & TMACl. Then the flask was quickly stoppered and the reaction was allowed to proceed for 1 hour at 60° C. In this example, azoxybenzene and 2-NDPA were obtained as reaction by-products that were not obtained with TMAH. So these byproducts were included in the calculation of selectivity.

Figure 5:
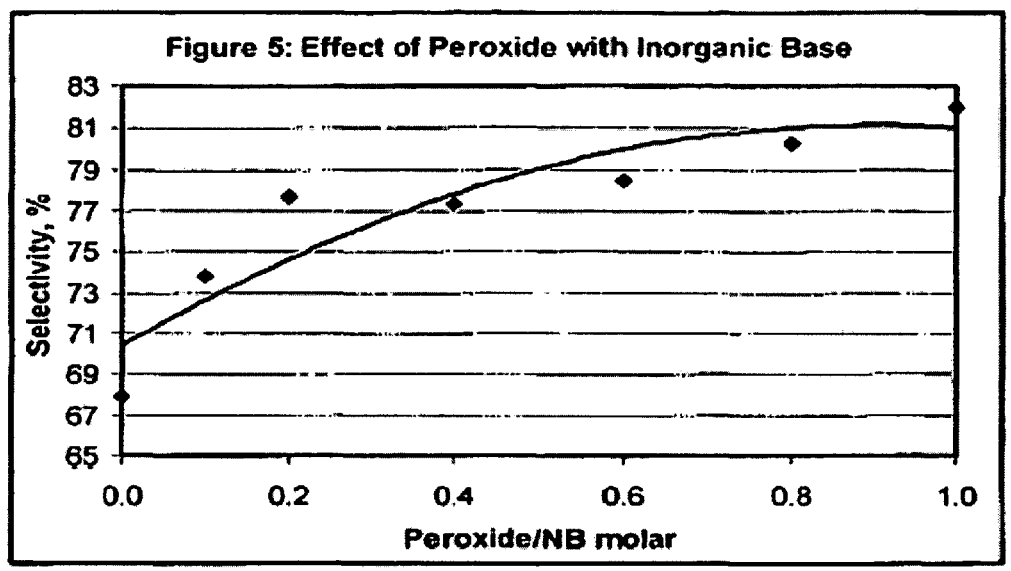
FIG. 5 is a graph showing the effect of peroxide with inorganic base as discussed in Comparative Example 2.

FIG. 5 shows that with a strong inorganic base and a phase transfer catalyst, selectivity increases steadily as the mole ratio of peroxide/NB is increased from 0 to unity. However, with a strong organic base, i.e. TMAH, there were optimum mole ratios with both fresh and recycle base. It is unexpected that there is an optimum mole ratio with a strong organic base, but not with a strong inorganic base and PTC that generate the same strong organic base in situ. Moreover, the inorganic system gave 2-NDPA+azoxybenzene levels of 1.1% to 2.4%, whereas none was formed with TMAH. Again, it is surprising that these by-products are formed with a strong inorganic base, but not with a strong organic base.

We claim:

1. A method of producing 4-aminodiphenylamine or a 4-aminodiphenylamine derivative, the method comprising the steps of:
   a. contacting an aniline or aniline derivative and nitrobenzene;
   b. reacting the aniline or aniline derivative and nitrobenzene in the presence of a strong organic base and an oxidant comprising hydrogen peroxide in an amount of about 0.01 to about 0.60 moles of hydrogen peroxide to moles of nitrobenzene to form a 4-aminodiphenylamine intermediate; and
   c. reducing the 4-aminodiphenylamine intermediate in a reduction reaction to produce 4-aminodiphenylamine.

2. The method of claim 1, wherein the aniline or aniline derivative and nitrobenzene are brought into contact in the presence of the strong base before contacting the aniline or aniline derivative and the nitrobenzene with the oxidant.

3. The method of claim 2, wherein the temperature of the aniline or aniline derivative and nitrobenzene is increased to at least about 65° C. prior to contact with the hydrogen peroxide.

4. The method of claim 1, wherein the aniline or aniline derivative is reacted with nitrobenzene at a molar ratio of aniline or aniline derivative to nitrobenzene of about 5.5 or lower.

5. The method of claim 1, further comprising the step of reductively alkylating the 4-aminodiphenylamine to form an alkylated derivative of the 4-aminodiphenylamine.

6. The method of claim 1, wherein the aniline or aniline derivative and nitrobenzene are reacted in a mixture comprising the strong organic base and the oxidant comprising hydrogen peroxide in an amount of from about 0.01 to about 0.20 moles of hydrogen peroxide per mole of nitrobenzene.

7. The method of claim 6, wherein the mixture comprises from about 0.020 to about 0.064 moles of the hydrogen peroxide per mole of nitrobenzene.

8. The method of claim 1, wherein the reaction temperature in step (b) is from about 65° C. to about 90° C.

9. The method of claim 1, wherein the hydrogen peroxide is supplied as an aqueous solution comprising from about 3 wt. % to about 5 wt. % hydrogen peroxide.

10. The method of claim 1, wherein the strong base is tetramethylammonium hydroxide.

11. The method of claim 1, wherein the hydrogen peroxide is supplied as an aqueous solution comprising from about 3 wt. % to about 7 wt. % hydrogen peroxide in an amount of from about 0.01 to about 0.5 moles of hydrogen peroxide to moles of nitrobenzene.

12. The method of claim 1, wherein the hydrogen peroxide is supplied as an aqueous solution comprising from about 15 wt. % to about 25 wt. % hydrogen peroxide in an amount of from about 0.01 to about 0.45 moles of hydrogen peroxide to moles of nitrobenzene.

13. The method of claim 1 wherein the hydrogen peroxide is supplied as an aqueous solution comprising from about 25 wt. % to about 40 wt. % hydrogen peroxide in an amount of from about 0.01 to about 0.35 moles of hydrogen peroxide to moles of nitrobenzene.

14. The method of claim 1, wherein the strong base is recycled from the products of the reduction reaction and contacted with the aniline or aniline derivative and nitrobenzene.

15. The method of claim 14, wherein the nitrobenzene has a feed time of about 100 minutes or less.

16. The method of claim 15 wherein the reaction temperature is from about 65° to about 90° C.

17. A method of producing a rubber product comprising the steps of:
   a. contacting an aniline or aniline derivative and nitrobenzene;
   b. reacting the aniline or aniline derivative and nitrobenzene in the presence of a strong organic base and an oxidant comprising hydrogen peroxide to form a 4-aminodiphenylamine intermediate in the absence of a strong inorganic base;
   c. reducing the 4-aminodiphenylamine intermediate in a reduction reaction to produce 4-aminodiphenylamine;
   d. reductively alkylating the 4-aminodiphenylamine to form an alkylated derivative of the 4-aminodiphenylamine; and
   e. incorporating the alkylated derivative of the 4-aminodiphenylamine into a rubber product.

18. The method of claim 17, wherein the aniline or aniline derivative and nitrobenzene are brought into contact in the presence of the strong base before contacting the aniline or aniline derivative and nitrobenzene with the oxidant.

19. The method of claim 17, wherein the aniline or aniline derivative is reacted with nitrobenzene at an aniline or aniline derivative to nitrobenzene molar ratio of 5.5 or lower.

20. A composition comprising aniline or aniline derivative, nitrobenzene, a strong organic base in the absence of a strong inorganic base and hydrogen peroxide in an amount of about 0.01 to about 0.60 moles of hydrogen peroxide to moles of nitrobenzene.

21. The composition of claim 20, where the composition further comprises water.

22. The composition of claim 21, where the composition comprises no more than about 0.35% wt phenazine.

23. The composition of claim 21, where the strong organic base comprises tetramethyammoniumhydroxide (TMAH).

24. The method of claim 17, where the hydrogen peroxide is supplied as an aqueous solution comprising from about 3 wt. % to about 50 wt. % hydrogen peroxide.

25. The method of claim 24, where the hydrogen peroxide is supplied in an amount of from about 0.01 to about 0.6 moles of hydrogen peroxide to moles of nitrobenzene.

26. A method of producing 4-aminodiphenylamine or a 4-aminodiphenylamine derivative, the method comprising the steps of:

a. contacting an aniline or aniline derivative and nitrobenzene;
b. reacting the aniline or aniline derivative and nitrobenzene in the presence of a strong organic base and an oxidant comprising hydrogen peroxide and supplied as an aqueous solution comprising from about 3 wt. % to about 50 wt. % hydrogen peroxide to form a 4-aminodiphenylamine intermediate; and
c. reducing the 4-aminodiphenylamine intermediate in a reduction reaction to produce 4-aminodiphenylamine.

27. The method of claim 26, where the hydrogen peroxide is provided in an amount of about 0.01 to about 0.60 moles of hydrogen peroxide to moles of nitrobenzene.

28. The method of claim 27, where the hydrogen peroxide and supplied as an aqueous solution comprising from about 15 wt. % to about 40 wt. % hydrogen peroxide and in an amount of about 0.04 to about 0.60 moles of hydrogen peroxide to moles of nitrobenzene.

* * * * *